United States Patent [19]

ogly Shakhtakhtinsky et al.

[11] 4,314,851
[45] Feb. 9, 1982

[54] ANTIFOULING COATING COMPOSITIONS

[76] Inventors: Togrul N. ogly Shakhtakhtinsky, ulitsa 28 Aprelya, 11. kv. 38, Baku; Zakir M. ogly Rzaev, 1 mikroraion, $1^b/6$, kv. 8, Sumgait; Svetlana G. kyzy Mamedova, ulitsa Avakiana, 45, kv. 22, Baku; Akhmed D. ogly Dunyamaliev, 13 mikroraion. 42, kv. 39, Sumgait; Mustafa S. ogly Salakhov, 1 kvartal, 24A, kv. 66, Sumgait; Mustafa M. ogly Guseinov, prospekt Narimanova, kvartal 522, G, kv. 30, Baku, all of U.S.S.R.

[21] Appl. No.: 179,977

[22] Filed: Aug. 21, 1980

Related U.S. Application Data

[62] Division of Ser. No. 11,039, Feb. 9, 1979, Pat. No. 4,261,914.

[51] Int. Cl.$^3$ ............................................... C09D 5/14
[52] U.S. Cl. ................................ 106/16; 106/18.35; 106/236; 106/241; 260/27 R; 260/33.6 EP; 260/33.6 UA; 260/37 EP; 260/42; 424/288
[58] Field of Search ...................... 106/16, 18.35, 236, 106/241; 424/288; 260/27 R, 33.6 EP, 33.6 UA, 37 EP, 42

[56] References Cited

U.S. PATENT DOCUMENTS

| | | | |
|---|---|---|---|
| 3,236,793 | 2/1966 | Robins et al. | 424/288 |
| 3,463,644 | 8/1969 | Hechenbleikner | 106/18.35 |
| 3,590,061 | 6/1971 | Minieri | 428/288 |
| 3,615,744 | 10/1971 | Yokoo | 106/16 |

*Primary Examiner*—Lorenzo B. Hayes
*Attorney, Agent, or Firm*—Lilling & Greenspan

[57] ABSTRACT

Proposed herein are antifouling coating compositions containing bis-trialkylstannyl derivatives of chlorinated polycyclic dicarboxylic acids, of the general formula

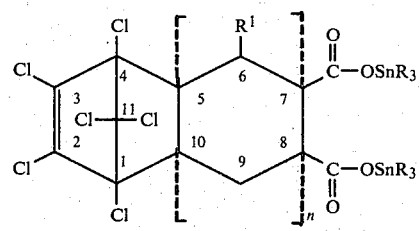

wherein R is a lower alkyl, R'=H,CH$_3$, n=0,1, which are obtained by a condensation reaction of anhydrides of the respective dicarboxylic acids with hexaalkyldistannoxanes R$_3$SnOSnR$_3$, wherein R is a lower alkyl, in the medium of an organic solvent.

6 Claims, No Drawings

ANTIFOULING COATING COMPOSITIONS

This is a division of application Ser. No. 11,039, filed Feb. 9, 1979, now U.S. Pat. No. 4,261,914.

FIELD OF THE INVENTION

The present invention relates to protection of the surfaces of various structures against marine fouling, and more particularly to bis-trialkylstannyl derivatives of chlorinated polycyclic dicarboxylic acids, to a method for producing same, and to compositions for antifouling coatings.

BACKGROUND OF THE INVENTION

It is well known that the accumulation of a great amount of a biomass on the surface of offshore installations, platforms and piles, as well as on ships' bottoms, causes serious biological problems and causes substantial damage. One effective way to protect various surfaces against marine fouling is the use of chemicals, namely, the application of protective polymer coatings containing antifouling agents.

An important stage in solving the fouling problem is the search for more effective antifouling agents. Organotin compounds are known to be widely employed as antifouling toxins in various polymer coatings.

The prior art antifouling polymer compositions contain, as the active component, organotin carboxylate compounds of the general formula R—COOSn(n—$C_4H_9$)$_3$ (wherein R is an alkyl, aryl), CCl=CCl—COOSnR$_3$ (wherein R is an alkyl), (cf. Japanese Patent Nos. 1,103, 1909, Cl. 24F1; 26,437, 1970, Cl. 24F1; 31,553, 1970, Cl. 24F1).

There has been proposed an antifouling composition with organotin toxins of the R$_3$SnX type (wherein R is an alkyl, aryl; X is a halogen) (cf. Japanese Patent No. 26,438, 1970, Cl. 24F2).

The "Takeda Chemical Ind. Ltd" compound has developed an antifouling polymeric paint containing, as the toxin, a synergistic mixture of aminochloronaphthoquinone, $Cu_2O$ and hexabutyldistannoxane [(n-$C_4H_9$)$_3$Sn]$_2$O or trialkylfluorostannane R$_3$SnF and bis-trialkylstannylmaleate R$_3$SnOOC—CH=CH—COOSnR$_3$ (cf. U.S. Pat. No. 3,615,744; Cl. 106/15 CO9d5/14; 1971).

The "Plastic Molders Supply Inc" compound has proposed a composition for protecting ships' bottoms and offshore installations against fouling, based on a polyester resin and an organotin compound (12–20%) of the R$_3$SnF type, wherein R is an alkyl, aryl (cf. French Pat. No. 2,055,996; Cl. CO9d5/00 1971).

To impart antifouling properties to paints, the "Caddsec Chemical Works Inc." company of the United States has proposed a composition containing organotin sulfur-containing compounds of the general formula [R$_3$SnOOC(CH$_2$)$_n$S]$_2$CH$_2$, wherein R is an alkyl (cf. U.S. Pat. No. 3,463,644; Cl. 106-15 (A61k); 1960).

A patent has been granted for a polymer material for an underwater antifouling coating, which contains high-molecular organotin compounds obtained by full or partial introduction of compounds of trialkyl(phenyl)tin, amines, isocyanates, etc. into the carboxyls of a dimeric acid (cf. Japanese Pat. No. 1,224/73; Cl. 24F21 (COd5/16), 1973).

Also proposed as antifouling agents have been organotin compounds of the (n-$C_4H_9$)$_3$SnXR type (wherein R is a halogenated phenyl, X=O,S) (cf. Japanese Pat. No. 48-41,258; Cl. 24F1, 1973) and of the (n-$C_4H_9$)$_3$SnX type (wherein X is toluene sulfoanilide) (cf. Japanese Pat. No. 37,491; Cl. 24f2, 1972).

There has been proposed a method for producing biostable paints and varnishes by way of modification of known polymers with organotin methacrylates, maleates and their polymers in combination with a binder, a filler, a solvent and other additives (cf. USSR Inventor's Certificate No. 210,296; Cl. 22h 10/01, 39b, 22/01 (CO9d, CO8f), 1967).

Also known are antifouling paints based on bis-(triphenyl-tin)-monochloromaleinate ($C_6H_5$)$_3$SnOOC—CH=CCl—COOSn($C_6H_5$)$_3$ (cf. Japanese Patent No. 51-41,648, 1976), compounds of the ($C_6H_5$)$_3$SnX type, wherein X=OH, F, Cl, OOCCH$_3$, OOCCH$_2$Cl, OSn($C_6H_5$)$_3$ or compounds of the formula ($C_6H_5$)$_3$ SnOOC-CH(Br)COOSn($C_6H_5$)$_3$ (cf. Japanese Pat. No. 51-109,934, 1976).

The above prior art organotin compounds used as antifouling agents suffer from a number of serious disadvantages, namely;

The process of producing these compounds is complex and involves numerous steps. Raw materials are scarce or unavailable.

Most organotin compounds are powders or solids with a pungent odor, which necessitates additional expenses and precautions when they are introduced into paints.

Organotin and chlororganic compounds are, when taken separately, less effective toxins against marine fouling. Halogen-containing agents suppress growth of organisms primarily of vegetal origin, while organotin toxins prevent accumulation of a biomass predominantly of animal origin.

The prior art organotin compounds are highly effective as antifouling agents, however their activity is short lived because of the high rate of their leaching out in sea water.

The prior art compounds are poorly soluble and compatible with known film-forming polymers, pigments and fillers used in antifouling coatings.

The prior art antifouling coatings with the above organotin compounds are not adequately adhesive and strong, and their weatherproof characteristics are poor.

SUMMARY OF THE INVENTION

It is, therefore, an object of the present invention to provide novel chlorinated organotin compounds featuring high antifouling activity, as well as antifouling polymer compositions based thereon.

According to the invention, there are proposed bis-trialkylstannyl derivatives of chlorinated polycyclic dicarboxylic acids, of the general formula (I)

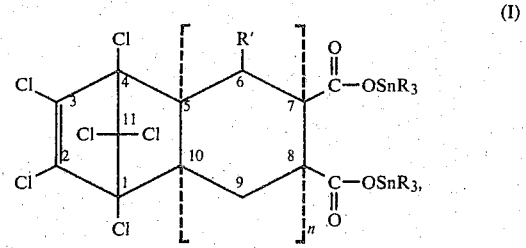

wherein R is a lower alkyl, R'=H, CH$_3$ and n=0,1.

Compounds of the above formula are novel substances.

It has been established that these compounds are biologically active and can be used as antifouling agents in protective polymer coatings.

DETAILED DESCRIPTION OF THE INVENTION

The proposed compounds are more effective antifouling agents than those known in the prior art and suppress growth of biomasses of both vegetal and animal origin. This property is due to the presence in the molecule of said compounds of chlorinated cyclic fragments with two organotin carboxyls. Another advantage of the proposed compounds is the low rate of their leaching out in sea water, which provides for a longer life of coatings based on them.

The most effective compounds are bis-tri-n-butylstannyl derivatives, owing to their adequate compatibility with polymeric binders and other ingredients of the compositions.

According to the invention, there are also proposed compositions for antifouling coatings, containing, as the active component, one of said organotin compounds, a polymeric binder, a filler, a pigment, a solvent and various additives in the following ratio, in parts by weight:

| | |
|---|---|
| active component: chlorinated organotin compound of formula (I) | 5–10 |
| binder | 7–30 |
| filler | 25–30 |
| pigment | 0.5–5.5 |
| additives | 0–5.5 |
| solvent | 10–35. |

The proposed composition may be of various types, depending on the active component used and other ingredients.

The preferable compositions in which the active component is compatible with the other ingredients are as follows:

| I. Composition with the following ratio of components, parts by weight: | |
|---|---|
| 1. Chlorinated organotin compound of the formula (I), wherein R = n-C₄H₉, R' = CH₃, n = 1 | 10.0 |
| 2. Copolymer of vinyl chloride and vinyl acetate | 17.0 |
| 3. Colophony | 12.0 |
| 4. Titanium white | 28.0 |
| 5. Toluene | 33.0. |

| II. Composition with the following ratio of components, parts by weight: | |
|---|---|
| 1. Chlorinated organotin compound of the formula (I), wherein R = n-C₄H₉, n = 0 | 10.0 |
| 2. Copolymer of vinyl chloride and vinyl acetate | 17.0 |
| 3. Colophony | 12.0 |
| 4. Titanium white | 28.0 |
| 5. Toluene | 33.0. |

| III. Composition with the following ratio of components, parts by weight: | |
|---|---|
| 1. Chlorinated organotin compound of the formula (I), wherein R = n-C₄H₉, R' = CH₃, n = 1 | 7.5 |
| 2. Postchlorinated polyvinyl chloride | 8.0 |
| 3. Colophony | 9.0 |
| 4. Zinc white | 30.0 |
| 5. Dibutylphthalate | 5.0 |
| 6. Salicylanilide | 5.5 |
| 7. Ethylacetate and toluene in a 1:1 ratio | 35.0. |

| IV. Composition with the following ratio of components, parts by weight: | |
|---|---|
| 1. Chlorinated organotin compound of the formula (I), wherein R = C₂H₅, R' = CH₃, n = 1 | 10.0 |
| 2. Epoxy resin | 30.0 |
| 3. Polyethylene polyamine | 5.0 |
| 4. Dibutylphthalate | 7.5 |
| 5. Zinc white | 30.0 |
| 6. Toluene | 12.5. |

The binders, fillers, pigments, solvents and other additives included in the proposed compositions are commercially available products.

The proposed compositions are produced by way of dispersing the respective components in a ball mill to a particle size of 60 to 70 microns. It takes 2 to 8 hours for the coatings to dry.

The above compositions for antifouling coatings, containing the proposed chlorinated organotin compounds of the above formula, exhibit superior performance characteristics such as antifouling activity, strength, adhesion and weatherproofness.

According to the invention, the method for producing compounds of the formula (I) comprises a condensation reaction of anhydrides of chlorinated polycyclic dicarboxylic acids of the formula (II)

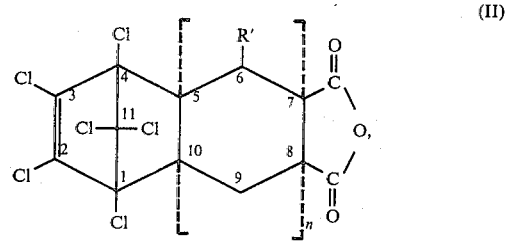

wherein R'=H, CH₃ and n=0.1, with hexaalkyldistannoxanes of the formula (III) R₃SnOSnR₃, wherein R is a lower alkyl, in the medium of an inert organic solvent. The reaction proceeds as follows:

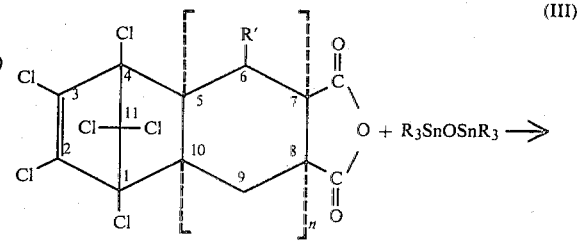

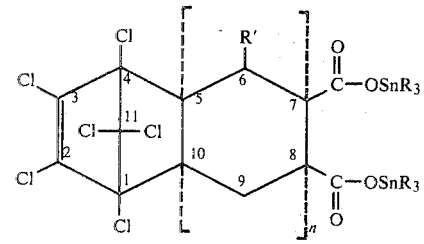

wherein R is a lower alkyl, R'=H,CH₃ and n=0,1.

The reaction is exothermic and occurs at room temperature, although at 60° to 80° C. it is more effective. The starting components may be taken in a stoichiometric ratio or with a slight excess of said anhydride. The resulting compounds are waxy or gummy products without any pungent odor and are readily soluble in organic solvents.

The starting components, i.e. anhydrides of chlorinated polycyclic dicarboxylic acids of the formula (II) and hexaalkyldistannoxanes of the formula (III) are well known and readily available compounds. The process for producing the composition can be easily implemented industrially.

Bearing in mind that the process for producing said compounds involves a single stage, can be conducted under mild conditions, does not require excessive power and additional reagent consumption, is simple and easy in implementation, and makes use of readily available starting components, the commercial value of the proposed compounds and antifouling compositions based thereon is obvious.

For a better understanding of the present invention specific examples of its practical embodiment are given by way of illustration, Examples 1 through 9 illustrating the obtaining of compounds and Examples 10 through 27, the obtaining of compositions on their basis.

EXAMPLE 1

Obtaining of bis-Trimethylstannyl Ester of 1,2,3,4,11,11-Hexachloro-6-methyltricyclo $(4,2,1,0^{5,10})$ undecene-2-dicarboxylic-7,8 Acid A four-necked flask provided with a mechanical stirrer, a condenser, a thermometer, a dropping funnel and a nitrogen inlet tube is charged with 6.6 g (0.015 g.M) of anhydride of 1,2,3,4,11,11-hexachloro-6-methyltricyclo $(4,2,1,0^{5,10})$undecene-2-dicarboxylic-7,8 acid and 200 ml of benzene. The mixture is stirred with heating at 60° C. till complete dissolution of the anhydride, then 3.4 g (0.01 g.M) of hexamethyldistannoxane dissolved in 10 ml of benzene are added into the reaction zone. The reaction is accompanied by heat evolution.

The reaction mixture is heated at 80° C. for 10 hours. The reaction product is isolated by extraction with heptane. Therewith, the excess amount of the unreacted anhydride precipitates, and the precipitate is separated by filtration. After distillation of the solvent and evacuation, the obtained product is dried in a vacuum desiccator at 40° C. 6.0 g (76% of the theoretical) of the product are obtained, with the following characteristics: melting point, 47.5° to 49° C.; molecular mass, 783.6 (determined by cryoscopy in benzene). Found, %: Cl 27.86, Sn 29.97. $C_{20}H_{28}O_4Cl_6Sn_2$. Calculated, %: Cl 27.18, Sn 30.33.

IR spectra, cm$^{-1}$: $\nu_{C-Cl}$ 680, $\nu_{Sn-C}^s$ 515, $\nu_{Sn-C}^{as}$ 610, $\nu_{C=O}$ 1790, 1830, 1595 (Me$_3$SnOOC-).

EXAMPLE 2

Obtaining of bis-Triethylstannyl Ester of 1,2,3,4,11,11-Hexachloro-6-methyltricyclo[4,2,1,0$^{5,10}$]undecene-2-dicarboxylic-7,8 Acid Under conditions similar to those of Example 1, from 52.7 g (0.12 g.M) of the anhydride of Example 1 and 42.7 g (0.1 g.M) of hexaethyldistannoxane there are obtained 71.0 g (82% of the theoretical) of a yellowish syrupy product with $\eta=612.5$ cS, molecular mass of 865.8, and $d_4^{20}=1.4855$. Found, %: Cl 24.75, Sn 27.26. $C_{26}H_{40}O_4Cl_6Sn_2$. Calculated, %: Cl 24.54, Sn 27.39.

IR spectra, cm$^{-1}$: $\nu_{C-Cl}$ 680, $\nu_{Sn-C}^s$ 505, $\nu_{Sn-C}^{as}$ 600, $\nu_{C=O}$ 1785, 1830, 1595 (Et$_3$SnOOC—).

EXAMPLE 3

Obtaining of bis-Tri-n-propylstannyl Ester of 1,2,3,4,11,11-Hexachloro-6-methyltricyclo[4,2,1,0$^{5,1-0}$]undecene-2-dicarboxylic-7,8 Acid Under conditions similar to those of Example 1, from 65.8 g (0.15. g.M) of the anhydride of Example 1 and 61.4 g (0.12 g.M) of hexa-n-propyldistannoxane there are obtained 97.5 g of the product in the form of a gummy light yellow mass. The yield is 85.5% of the theoretical, $\eta=457$ cS, molecular mass 950, $d_4^{20}=1.4220$. Found, %: Cl 22.07, Sn 25.18. $C_{32}H_{52}O_4Cl_6Sn_2$. Calculated, %: Cl 22.37, Cn 24.96.

Ir spectra, cm$^{-1}$: $\nu_{C-Cl}$ 685, $\nu_{Sn-C}^s$ 490, $\nu_{Sn-C}^{as}$ 600, $\nu_{C=O}$ 1790, 1825, 1595 (n-Pr$_3$SnOOC—).

EXAMPLE 4

Obtaining of bis-Tri-n-butylstannyl Ester of 1,2,3,4,11,11-Hexachloro-6-methyltricyclo[4,2,1,0$^{5,1-0}$]undecene-2-dicarboxylic-7,8 Acid Under conditions similar to those of Example 1, from 43.9 g (0.1 g.M) of the anhydride of Example 1 and 65.6 g (0.11 g.M) of hexa-n-butyldistannoxane there are obtained 91.3 g of a viscous light yellow product. The yield is 88.2 of the theoretical, $\eta=374.6$ cS, $d_4^{20}=1.3689$, molecular mass of 1,120. Found, %: Cl 20.85, Sn 23.24. $C_{38}H_{64}O_4Cl_6Sn_2$. Calculated, %: Cl 20.55, Sn 22.93.

IR spectra, cm$^{-1}$: $\nu_{C-Cl}$ 60, $\nu_{Sn-C}^s$ 490, $\nu_{Sn-C}^{as}$ 600, $\nu_{C=O}$ 1790, 1820, 1590 (n-Bu$_3$SnOOC—).

EXAMPLE 5

Obtaining of bis-Triethylstannyl Ester of 1,2,3,4,11,11-Hexachlorotricyclo-[4,2,1,0$^{5,10}$]undecene-2-dicarboxylic Acid Under conditions similar to those of Example 1, from 42.5 g (0.1 g.M) of anhydride of hexachlorotricycloundecene dicarboxylioacid and 42.7 g (0.1 g.M) of hexaethyldistannoxane there are obtained 65.4 g of a gummy light yellow product. The yield is 76.8% of the theoretical, $\eta=680$ cS, molecular mass of 850, $d_4^{20}=1.49.05$. Found, %: Cl 25.41, Sn 26.34. $C_{25}H_{38}O_4Cl_6Sn_2$. Calculated, %: Cl 24.97, Sn 27.83.

IR spectra, cm$^{-1}$: $\nu_{Sn-C}^s$ 510, $\nu_{Sn-C}^{as}$ 615, $\nu_{C-Cl}$ 680, $\nu_{C=O}$ 1785, 1835, 1590 (Et$_3$SnOOC—), $\nu_{C=O}$ 1600.

EXAMPLE 6

Obtaining of bis-Tri-n-butylstannyl Ester of 1,2,3,4,11,11-Hexachlorotoricyclo 4,2,1,0$^{5,10}$undecene-2-dicarboxylic-7,8 Acid Under conditions similar to those of Example 1, from 42.5 g (0.1 g.M) of the anhydride of Example 5 and 59.5 g (0.1 g.M) of hexa-n-butyldistannoxane there are obtained 84.2 of a gummy transparent mass. The yield is 82.5%, $\eta=390$cS, $d_4^{20}=1.3710$, molecular mass of 1,015. Found, %: Cl 21.61, Sn 22.96, $C_{39}H_{62}O_4Cl_6Sn_2$. Calculated, %: Cl 21.09, Sn 23.50.

IR spectra, cm$^{-1}$: $\nu_{C-Cl}$ 685, $\nu_{Sn-C}^s$ 495, $\nu_{Sn-C}^{as}$ 605, $\nu_{C=O}$ 1790, 1815, 1505 (n-Bu$_3$SnOOC—).

EXAMPLE 7

Obtaining of bis-Triethylstannyl Ester of 1,2,3,4,7,7-Hexachlorobicyclo-[2,2,1]heptene-2-dicarboxylic-5,6 Acid Under conditions similar to those of Example 1, from 44.5 g (0.12 g.M) of chlorendic anhydride and 42.7 g (0.1 g.M) of hexaethyldistannoxane there are obtained 71.4 g of a waxy light yellow product. The yield is 89.5%, melting point of 74.5° C., molecular mass of 800. Found, %: Cl 27.08, Sn 30.19. $C_{21}H_{32}O_4Cl_6Sn_2$. Calculated, %: Cl 26.29, Sn 29.73.

IR spectra, cm$^{-1}$: $\nu_{C-Cl}$ 680, $\nu_{Sn-C}{}^s$ 510, $\nu_{Sn-C}{}^{as}$ 610, $\nu_{C=O}$ 1780, 1840, 1595 (Et$_3$SnOOC—).

EXAMPLE 8

Obtaining of bis-Tri-n-propylstannyl Ester of 1,2,3,4,7,7-Hexachlorolicyclo-[2,2,1]-heptene-2-dicarboxylic-5,6 Acid Under conditions similar to those of Example 1, from 44.5 g (0.12 g.M) of chlorendic anhydride and 51.1 g (0.1 g.M) of hexapropyldistannoxane there are obtained 79.4 g of a gummy product. The yield is 90%, $\eta=810$ cS, $d_4^{20}=1.4130$, molecular mass of 885. Found, %: Cl 24.75, Sn 27.22. $C_{27}H_{44}O_4Cl_6Sn_2$. Calculated, %: Cl 24.15, Sn 26.98.

IR spectra, cm$^{-1}$: $\nu_{C-Cl}$ 675, $\nu_{Sn-C}{}^s$ 500, $\nu_{Sn-C}{}^{as}$ 600, $\nu_{C=O}$ 1770, 1840, 1590 (Pr$_3$SnOOC-), $\nu_{C=C}$ 1600.

EXAMPLE 9

Obtaining of bis-Tri-n-butylstannyl Ester of Chlorendic Acid

Under conditions similar to those of Example 1, from 89 g (0.24 g.M) of chlorendic anhydride and 119 g (0.2 g.M) of hexan-butyldistannoxane there are obtained 178.7 g of a product in the form of a viscous resinous mass. The yield is 92.5%, $\eta=720$ cS, $d_4^{20}=1.3926$, $n_D^{20}=1.5281$, molecular mass of 970. Found, %: Cl 21.86, Sn 25.11. $C_{33}H_{56}Cl_6Sn_2$. Calculated, %: Cl 22.05, Sn 24.56.

IR spectra, cm$^{-1}$: $\nu_{C-Cl}$ 680, $\nu_{Sn-C}{}^s$ 490, $\nu_{Sn-C}{}^{as}$ 615, $\nu_{C=O}$ 1785, 1830, 1590 (n-Bu$_3$SnOOC—).

The following examples illustrate compositions for antifouling coatings.

EXAMPLE 10

Composition containing a Compound of the Formula (I), Wherein R=n-C$_4$H$_9$, R'=CH$_3$, n=1, Obtained As Described in Example 4

Charged into a ball mill are 10 parts by weight of said chlorinated organotin compound, 17.0 parts by weight of a copolymer of vinyl chloride and vinyl acetate, 12 parts by weight of colophony, 28 parts by weight of titanium white and 33 parts by weight of toluene. The charge is milled to a suspended particle size of 70 microns. The resulting composition is ready for use as antifouling coatings and can be applied by any conventional technique, such as spraying, application with a brush or a roller, etc. As a result, a uniform, durable matte coat 40 to 50 microns thick is formed. It takes 6 hours for the coating to dry. The properties of the coating are listed in Table 1.

EXAMPLE 11

Composition Containing a Compound of the Formula (I), Wherein R=n-C$_4$H$_9$, R'=H, n=1, Obtained As Described in Example 6

Under conditions similar to those of Example 10, there is prepared a composition with the following ratio of components, parts by weight:

| chlorinated organotin compound of the Formula (I), | |
|---|---|
| wherein R = n-C$_4$H$_9$, R' = H, n = 1 | 10.0 |
| copolymer of vinyl chloride and vinyl acetate | 17.0 |
| colophony | 12.0 |
| titanium white | 28.0 |
| toluene | 33.0 |

The properties of the coating are listed in Table 1.

EXAMPLE 12

Composition Containing a Compound of the Formula (I), Wherein R=n-C$_4$H$_9$, n=0, Obtained As Described in Example 9

Under conditions similar to those of Example 10, there is prepared a composition with the following ratio of components, parts by weight:

| chlorinated organotin compound of the formula (I), | |
|---|---|
| wherein R = n-C$_4$H$_9$, n = 0 | 10.0 |
| copolymer of vinyl chloride and vinyl acetate | 17.0 |
| colophony | 12.0 |
| titanium white | 28.0 |
| toluene | 3.0. |

The properties of the coating are listed in Table 1.

EXAMPLE 13

Composition Containing a Compound of the Formula (I), Wherein R=n-C$_4$H$_9$, R'=CH$_3$, n=1, Obtained As Described in Example 4

Under conditions similar to those of Example 10, there is prepared a composition with the following ratio of components, parts by weight:

| chlorinated organotin compound of the formula (I), | |
|---|---|
| wherein R = n-C$_4$H$_9$, R' = CH$_3$, n = 1 | 7.5 |
| postchlorinated polyvinyl chloride | 8.0 |
| colophony | 9.0 |
| zinc white | 30.0 |
| dibutylphthalate | 5.0 |
| salicylanilide | 5.5 |
| ethylacetate and toluene in a 1:1 ratio | 35.0. |

The properties of the coating are listed in Table 1.

EXAMPLE 14

Composition Containing a Compound of the Formula (I), Wherein R=n-C$_4$H$_9$, R'=H, n=1, Obtained As Described in Example 6

Under conditions similar to those of Example 19, there is prepared a composition with the following ratio of components, parts by weight:

| chlorinated organotin compound of the formula (I), | |
|---|---|
| wherein R = n-C$_4$H$_9$, R' = H, n = 1 | 7.5 |
| postchlorinated polyvinyl chloride | 8.0 |
| colophony | 9.0 |

-continued

| | |
|---|---|
| Zinc white | 30.0 |
| dibutylphthalate | 5.0 |
| salicylanilide | 5.5 |
| ethylacetate and toluene in a 1:1 ratio | 35.0 |

The properties of the coating are listed in Table 1.

EXAMPLE 15

Composition Containing a Compound of the Formula (I), Wherein R=n-C$_4$H$_9$, n=0, Obtained As Described in Example 9

Under conditions similar to those of Example 10, there is prepared a composition with the following ratio of components parts by weight:

| | |
|---|---|
| chlorinated organotin compound of the formula (I), wherein R = n-C$_4$H$_9$, n = 0 | 7.5 |
| postchlorinated polyvinyl chloride | 8.0 |
| colophony | 9.0 |
| zinc white | 30.0 |
| dibutylphthalate | 5.0 |
| salicylanilide | 5.5 |
| ethylacetate and toluene in a 1:1 ratio | 35.0 |

The properties of the coating are listed in Table 1.

EXAMPLE 16

Composition Containing a Compound of the Formula (I), Wherein R=n-C$_4$H$_9$, R'=CH$_3$, n=1, Obtained As Described in Example 4

Under conditions similar to those of Example 10, there is prepared a composition with the following ratio of components, parts by weight: chlorinated organotin compound of the formula (I),

| | |
|---|---|
| wherein R = n-C$_4$H$_9$, R' = CH$_3$, n = 1 | 10.0 |
| epoxy resin | 30.0 |
| polyethylene polyamine | 5.0 |
| dibutylphthalate | 7.5 |
| zinc white | 30.0 |
| toluene | 12.0 |

The properties of the coating are listed in Table 1.

EXAMPLE 17

Composition Containing a Compound of the Formula (I), Wherein R=n-C$_4$H$_9$, n=0, Obtained As Described in Example 9

Under conditions similar to those of Example 10, there is prepared a composition with the following ratio of components, parts by weight:

| | |
|---|---|
| chlorinated organotin compound of the formula (I), wherein R = n-C$_4$H$_9$, n = 0 | 10.0 |
| epoxy resin | 30.0 |
| polyethylene polyamine | 5.0 |
| dibutylphthalate | 7.5 |
| zinc white | 30.0 |
| toluene | 12.5 |

The properties of the coating are listed in Table 1.

EXAMPLE 18

Composition Containing a Compound of the Formula (I), Wherein R=CH$_3$, R'=CH$_3$, n=1, Obtained As Described in Example 1

Under conditions similar to those of Example 10, there is prepared a composition with the following ratio of components, parts by weight:

| | |
|---|---|
| chlorinated organotin compound of the formula (I), wherein R = CH$_3$, R' = CH$_3$, n = 1 | 10.0 |
| epoxy resin | 30.0 |
| polyethylene polyamine | 5.0 |
| dibutylphthalate | 7.5 |
| zinc white | 30.0 |
| toluene | 12.5 |

The properties of the coating are as follows: impact strength, 70 kg/cm; bending strength, 1 mm; pendulum hardness, 0.35; Weathering stability, 8 points; duration of antifouling action, 18 months.

EXAMPLE 19

Composition Containing a Compound of the Formula (I), Wherein R=C$_2$H$_5$, R'=CH$_3$, n=1, Obtained As Described in Example 2

Under conditions similar to those of Example 10, there is prepared a composition with the following ratio of components, parts by weight:

| | |
|---|---|
| chlorinated organotin compound of the formula (I), wherein R = C$_2$H$_5$, R' = CH$_3$, n = 1 | 10.0 |
| epoxy resin | 30.0 |
| polyethylene polyamine | 5.0 |
| dibutylphthalate | 7.5 |
| zinc white | 30.0 |
| toluene | 12.5 |

The properties of the coating are as follows: impact strength, 75 kg/cm; bending strength, 1 mm; hardness, 0.25; weathering stability, 7 points; duration of antifouling action, 20 months.

EXAMPLE 20

Composition Containing a Compound of the Formula (I), Wherein R=n-C$_3$H$_7$, R'=CH$_3$, n=1, Obtained As Described in Example 3

Under conditions similar to those of Example 10, there is prepared a composition with the following ratio of components, parts by weight:

| | |
|---|---|
| chlorinated organotin compound of the formula (I), wherein R = n-C$_3$H$_7$, R' = CH$_3$, n = 1 | 10.0 |
| epoxy resin | 30.0 |
| polyethylene polyamine | 5.0 |
| dibutylphthalate | 7.5 |
| zinc white | 30.0 |
| toluene | 12.5 |

The properties of the coating are as follows: impact strength, 80 kg/cm; bending strength, 1 mm; hardness, 0.3; weathering stability, 8 points; duration of antifouling action, 20 months.

EXAMPLE 21

Composition Containing a Compound of the Formula (I), Wherein $R=C_2H_5$, $R'=H$, $n=1$, Obtained As Described in Example 5

Under conditions similar to those of Example 10, there is prepared a composition with the following ratio of components, parts by weight:

| | |
|---|---|
| chlorinated organotin compound of the formula (I), wherein $R = C_2H_5$, $R' = H$, $n = 1$ | 10.0 |
| epoxy resin | 30.0 |
| polyethylene polyamine | 5.0 |
| dibutylphthalate | 7.5 |
| zinc white | 30.0 |
| toluene | 12.5 |

The properties of the coating are as follows: impact strength, 65 kg/cm; bending strength, 1 mm; hardness, 0.18; weathering stability, 7 points; duration of antifouling action, 18 months.

EXAMPLE 22

Composition Containing a Compound of the Formula (I), Wherein $R=C_2H_5$, $n=0$, Obtained As Described in Example 7

Under conditions similar to those of Example 10, there is prepared a composition with the following ratio of components, parts by weight:

| | |
|---|---|
| chlorinated organotin compound of the formula (I), wherein $R = C_2H_5$, $n = 0$ | 10.0 |
| epoxy resin | 30.0 |
| polyethylene polyamine | 5.0 |
| dibutylphthalate | 7.5 |
| zinc white | 30.0 |
| toluene | 12.5 |

The properties of the coating are as follows: impact strength, 80 kg/cm; bending strength, 1 mm; hardness, 0.15; weathering stability, 7 points; duration of antifouling action, 20 months.

EXAMPLE 23

Composition Containing a Compound of the Formula (I), Wherein $R=C_3H_7$, $n=0$, Obtained As Described in Example 8

Under conditions similar to those of Example 10, there is prepared a composition with the following ratio of components, parts by weight:

| | |
|---|---|
| chlorinated organotin compound of the formula (I), wherein $R = C_3H_7$, $n = 0$ | 10.0 |
| epoxy resin | 30.0 |
| polyethylene polyamine | 5.0 |
| dibutylphthalate | 7.5 |
| zinc white | 30.0 |
| toluene | 12.5 |

The properties of the coating are as follows: impact strength, 70 kg/cm; bending strength, 1 mm; hardness, 0.25; weathering stability, 8 points; duration of antifouling action, 20 months.

EXAMPLE 24

Composition Containing a Compound of the Formula (I), Wherein $R=C_2H_5$, $R'=CH_3$, $n=1$, Obtained As Described in Example 2

Under conditions similar to those of Example 10, there is prepared a composition with the following ratio of components, parts by weight:

| | |
|---|---|
| chlorinated organotin compound of the formula (I), wherein $R = C_2H_5$, $R' = CH_3$, $n = 1$ | 7.5 |
| postchlorinated polyvinyl chloride | 8.0 |
| colophony | 9.0 |
| zinc white | 30.0 |
| dibutylphthalate | 5.0 |
| salicylanilide | 5.5 |
| ethylacetate and toluene in a 1:1 ratio | 35.0 |

The properties of the coating are as follows: impact strength, 50 kg/cm; bending strength, 1 mm; hardness, 0.15; weathering stability, 7 points; duration of antifouling action, 18 months.

EXAMPLE 25

Composition Containing a Compound of the Formula (I), Wherein $R=C_2H_5$, $n=0$, Obtained As Described in Example 7

Under conditions similar to those of Example 10, there is prepared a composition with the following ratio of components, parts by weight:

| | |
|---|---|
| chlorinated organotin compound of the formula (I), wherein $R = C_2H_5$, $n = 0$ | 7.5 |
| postchlorinated polyvinyl chloride | 8.0 |
| colophony | 9.0 |
| zinc white | 30.0 |
| dibutylphthalate | 5.0 |
| salicylanilide | 5.5 |
| acetone and toluene in a 1:1 ratio | 35.0 |

The properties of the coating are as follows: impact strength, 55 kg/cm; bending strength, 1 mm; hardness, 0.16; weathering stability, 7 points; duration of antifouling action, 22 months.

EXAMPLE 26

Composition Containing a Compound of the Formula (I), Wherein $R=C_2H_5$, $n=0$, Obtained As Described in Example 7

Under conditions similar to those of Example 10, there is prepared a composition with the following ratio of components, parts by weight:

| | |
|---|---|
| chlorinated organotin compound of the formula (I), wherein $R = C_2H_5$, $n = 0$ | 10.0 |
| copolymer of vinyl chloride and vinyl acetate | 17.0 |
| colophony | 12.0 |
| titanium white | 28.0 |
| toluene | 33.0 |

The properties of the coating are as follows: impact strength, 50 kg/cm; bending strength, 1 mm; hardness, 0.2; weathering stability, 8 points; duration of antifouling action, 24 months.

EXAMPLE 27

Composition Containing a Compound of the Formula (I), Wherein R=C₂H₅, R'=CH₃, n=1, Obtained As Described in Example 2

Under conditions similar to those of Example 10, there is prepared a composition with the following ratio of components, parts by weight:

| | |
|---|---|
| chlorinated organotin compound of the formula (I), wherein R = C₂H₅, R' = CH₃, n = 1 | 7.5 |
| postchlorinated polyvinyl chloride | 8.0 |
| colophony | 9.0 |
| zinc white | 30.0 |
| dibutylphthalate | 5.0 |
| salicylanilide | 5.5 |
| acetone and toluene in a 1:1 ratio | 35.0 |

The properties of the coating are as follows: impact strength, 55 kg/cm; bending strength, 1 mm; hardness, 0.15; weathering stability, 7 points; duration of antifouling action, 18 months.

The properties of coatings from the compositions described in Examples 10 through 17 are listed in Table 1. For comparison, there are also given data for a prior art composition with active component (C₄H₉)₃SnOSn(C₄H₉)₃. As can be seen from Table 1, coatings from the proposed compositions exhibit sufficiently high performance characteristics.

Coatings containing the proposed chlorinated organotin compounds, applied on steel and aluminum plates 40×60 cm in size have been tested in sea water under natural conditions, in a region of intensive fouling, at a depth of 4 to 5 m.

The test results are summarized in Table 2.

What is claimed is:

1. In an antifouling coating composition comprising an antifouling agent, a polymeric binder, a filler, a pigment, and a solvent, the improvement comprising as the antifouling agent, a bis-trialkylstannyl derivative of chlorinated polycyclic dicarboxylic acids, having the general formula (I)

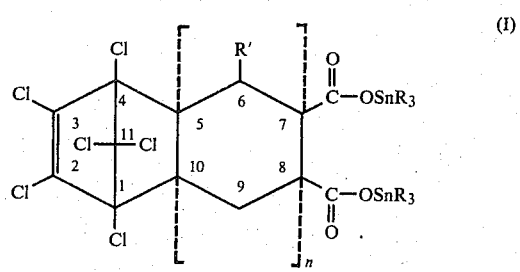

where R is a lower alkyl, R' is H or CH₃, and n is 0 or 1.

2. The composition of claim 1 having the following components, in parts by weight:

| | |
|---|---|
| antifouling agent | 5–10 |
| binder | 7–30 |
| filler | 25–30 |
| pigment | 0.5–5.5 |
| solvent | 10–35 |

3. A composition as claimed in claim 1, containing the following components, parts by weight:

| | |
|---|---|
| chlorinated organotin compound of the formula (I), wherein R = n-C₄H₉, R' = CH₃, n = 1 | 10.0 |
| copolymer of vinyl chloride and vinyl acetate | 17.0 |
| colophony | 12.0 |

TABLE 1

Properties of Antifouling Coatings Based on Various Compositions

| Properties of Coatings | Compositions for antifouling coatings as per Examples | | | | | | | | Prior art coating with toxin (C₄H₉)₃SnOSn(C₄H₉)₃ |
|---|---|---|---|---|---|---|---|---|---|
| | 10 | 11 | 12 | 13 | 14 | 15 | 16 | 17 | |
| 1. Impact strength, kg/cm | 50 | 50 | 55 | 50 | 55 | 55 | 70 | 70 | 50 |
| 2. Bending strength, mm | 1 | 1 | 1 | 1 | 1 | 1 | 1 | 1 | 2 |
| 3. Hardness, kg/sq.mm | 0.15 | 0.15 | 0.17 | 0.16 | 0.18 | 0.25 | 0.15 | 0.25 | 0.35 |
| 4. Cross-cut adhesion | 1 | 1 | 1 | 1 | 1 | 1 | 0.0 | 0.0 | 2 |
| 5. Particle size, microns | 70 | 60 | 65 | 70 | 70 | 70 | 70 | 65 | 50 |
| 6. Weathering stability, points | 7 | 7 | 7 | 8 | 7 | 8 | 8 | 8 | 2 |
| 7. Duration of antifouling action, months | 18 | 18 | 22 | 18 | 20 | 24 | 20 | 18 | 12 |
| 8. Drying time, hrs | 6 | 7 | 8 | 2 | 3 | 2 | 2 | 2 | 8 |

TABLE 2

Antifouling Activity of Chlorinated Organotin Compounds of the General Formula (I)

| R | R' | n | Leaching rate, mg/sq.cm per day | Degree of fouling, kg/sq.m Test duration, months | | | | Note |
|---|---|---|---|---|---|---|---|---|
| | | | | 6 | 12 | 18 | 24 | |
| CH₃ | CH₃ | 1 | 0.067 | 0.011 | 0.018 | 0.115 | 0.215 | On test specimens without |
| C₂H₅ | CH₃ | 1 | 0.051 | 0.009 | 0.015 | 0.095 | 0.155 | coating, a large amount |
| C₂H₅ | H | 1 | 0.049 | 0.009 | 0.016 | 0.105 | 0.165 | of biomass, 10 to 15 kg/sq |
| C₂H₅ | — | 0 | 0.031 | 0.01 | 0.105 | 0.165 | 0.205 | m over 6 to 8 months, |
| n-C₃H₇ | CH₃ | 1 | 0.038 | 0.008 | 0.014 | 0.095 | 0.18 | has been accumulated. |
| n-C₄H₉ | CH₃ | 1 | 0.027 | 0.005 | 0.09 | 0.11 | 0.145 | |
| n-C₄H₉ | H | 1 | 0.025 | 0.005 | 0.08 | 0.12 | 0.135 | |
| n-C₄H₉ | — | 0 | 0.028 | 0.003 | 0.06 | 0.095 | 0.125 | |
| (C₄H₉)₃SnOSn(C₄H₉)₃ (prior art) | | | 0.68 | 0.125 | 0.75 | 1.15 | 1.86 | |

4. A composition as claimed in claim 1, containing the following components, parts by weight:

| | |
|---|---|
| chlorinated organotin compound of the formula (I), wherein R = n-C$_4$H$_9$, n = 0 | 10.0 |
| copolymer of vinyl chloride and vinyl acetate | 17.0 |
| colophony | 12.0 |
| titanium white | 28.0 |
| toluene | 33.0. |

5. A composition as claimed in claim 1, containing the following components, parts by weight:

| | |
|---|---|
| chlorinated organotin compound of the formula (I), wherein R = n-C$_4$H$_9$, R' = CH$_3$, n = 1 | 7.5 |
| postchlorinated polyvinyl chloride | 8.0 |
| colophony | 9.0 |
| zinc white | 30.0 |
| dibutylphthalate | 5.0 |
| salicylanilide | 5.5 |
| ethylacetate and toluene in a 1:1 ratio | 35.0. |

6. A composition as claimed in claim 1, containing the following components, parts by weight:

| | |
|---|---|
| chlorinated organotin compound of the formula (I), wherein R = C$_2$H$_5$, R' = CH$_3$, n = 1 | 10.0 |
| epoxy resin | 30.0 |
| polyethylene polyamine | 5.0 |
| dibutylphthalate | 7.5 |
| zinc white | 30.0 |
| toluene | 12.5 |

\* \* \* \* \*